United States Patent [19]
Kuo et al.

[11] Patent Number: 5,679,861
[45] Date of Patent: Oct. 21, 1997

[54] $C_{60}$ DIAMINE ADDUCTS AND PREPARATION AND POLYMERS THEREOF

[75] Inventors: Tung-Ying Kuo; Jih-Ru Hwu, both of Hsinchu; Tsong-Ming Chang, Taipei, all of Taiwan

[73] Assignee: Industrial Technology Research Institute, Hsinchu, Taiwan

[21] Appl. No.: 481,111

[22] Filed: Jun. 7, 1995

[51] Int. Cl.⁶ .............................................. C07C 211/36
[52] U.S. Cl. .............................................. 564/458; 564/461
[58] Field of Search .............................................. 564/457, 458, 564/461

*Primary Examiner*—Brian M. Burn
*Attorney, Agent, or Firm*—W. Wayne Liauh

[57] ABSTRACT

The present invention is directed to $C_{60}$ diamine adducts, processes for preparing them and polymers prepared from them. $C_{60}$ diamine adducts is a symmetrical icosahegron which is composed of 12 pentagons and 20 hexagons and links to 2 to 4 diamines. The processes for preparing the product comprises the steps of: adding $C_{60}$ in benzene or toluene of a constant concentration to a certain amount of linear aliphatic diamine having the structural formula $H_2N-(CH_2)n-NH_2$ wherein n=2, 4 or 6 for reaction, or adding a definite amount of $C_{60}$ directly to linear diamine of a definite concentration to produce $C_{60}$ diamine adducts. Elemental analysis shows that the product contain about 5.9% nitrogen, about 72.6% carbon and about 3.84% hydrogen, and the number of diamine linked to $C_{60}$ is in the range of 2 to 4. $C_{60}$ diamine is useful as a polymerization monomer for the preparation of polyamides or relevant polymers.

9 Claims, 10 Drawing Sheets

$C_{60}$ DIAMINE ADDUCTS AND PREPARATION AND POLYMERS THEREOF

FIELD OF THE INVENTION

The present invention is directed to $C_{60}$ diamine adducts, processes for preparing them and polymers prepared from them. In particular, the present invention is directed to a process for preparing $C_{60}$ diamine adducts by reacting $C_{60}$ in benzene or toluene of a constant concentration with a definite amount of linear diamine under suitable conditions.

BACKGROUND OF DISCLOSURE $C_{60}$ is a relatively stable material exhibiting a variety of properties. It is a hollow molecule composed of pure carbon atoms and is in structure an icosahedron composed of 12 pentagons and 20 hexagons. $C_{60}$ is the main product of a high temperature vaporization of solid graphite rods by resistive heating or arc heating in the presence of a few torr of rare gas. $C_{60}$ can be prepared by dissolution of the soot in a solvent and extraction from the solution. Physical characterization shows that $C_{60}$ is heat resistant and active in reactions such as polymerization and addition.

SUMMARY OF THE INVENTION $C_{60}$ diamine adducts obtained in the present invention are useful as polymerization monomer, and can polymerize with dicarboxylic acids such as adipic acid, dicarboxylic esters such as methyl adipate or adipyl chloride such as dichlorodiamide to produce polyamide polymers or copolymers thereof.

One aspect of the present invention is to provide a process for preparing $C_{60}$ diamine adducts. The product prepared by the process of the present invention exhibits better heat resistance and electrophilic reactivity than conventional diamine adducts. Another aspect of the present invention is to provide a process for preparing $C_{60}$ diamine adducts by using linear diamine and $C_{60}$ (in solid form) or $C_{60}$ in benzene or toluene as starting materials.

One further aspect of the present invention is to provide $C_{60}$ diamine adducts prepared by the processes of the present invention which are useful as polymerization monomer for preparing polyamides and relavant polymers.

A still further aspect of the present invention is to show the results of the processes of the present invention. The reactions can be detected by infrared. Elemental analysis show that the product contains about 5.9% nitrogen, about 72.6% carbon and about 3.84% hydrogen and the number of diamine 5 linked to $C_{60}$ is approximatly in the range of 2 to 4.

DETAILED DESCRIPTION OF THE INVENTION

Figure 1:
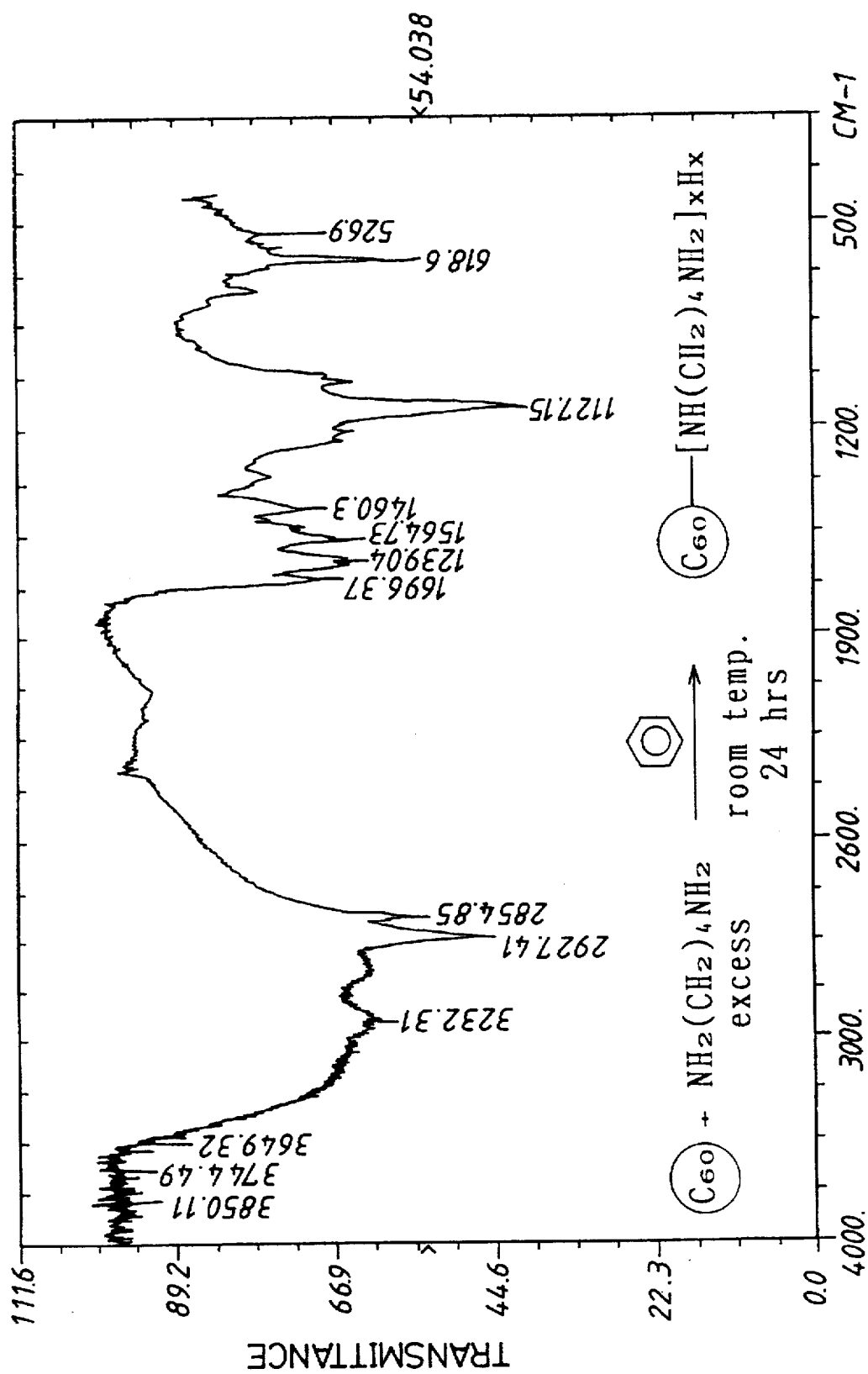
FIG. 1 shows the IR chromatogram obtained from the product of Example 1 illustrating the formation of $C_{60}$ diamine adduct.

The processes of the present inveniton mainly comprise reacting a definite amount of linear diamine with $C_{60}$ or $C_{60}$ in benzene or toluene. The processes of the present invention include:

(i) At room temperature and in nitrogen atmosphere, an excess amount (about 5000 to 10,000 equivalents) of 1,4 diaminobutane is added to $C_{60}$ in benzene for reaction. Deposite formation is observed while the color of solution gradually turns from purple to brown. The solution is sufficiently stirred to complete the reaction. After the completion of reaction, the solution is centrifuged and the pellet is obtained. The solid pellet is washed with water, methanol, acetone, toluene, and ether. After drying in vacuum, $C_{60}$ diamine adduct is obtained as brown-coffee powder. The reaction equation is as follows:

(ii) At reflux temperature and in nitrogen atmosphere, suitable amount of 1,6-diaminohexane is added to a definite amount of $C_{60}$ in toluene at slow reflux. Reflux is continued until the completion of reaction while the color of solution turns to brown and no more precipitate forms. The solvent is removed in a rotary evoporator. The residual precipitate is then washed with water, methanol, chloroform, acetone and ether. After drying in vacuum, $C_{60}$ diamine adduct is obtained as brown-coffee powder. The reaction equation is as follows:

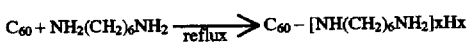

(iii) In this process, suitable amount of 1,6-diaminohexane and an excess amount of carbon and benzene are added to a flask. The mixture is vigorously stirred in nitrogen atmosphere and ultrasonicated for several hours. After the completion of reaction, the precipitate is seperated by centrifugation and washed with water, methanol, acetone and ether. After drying in vacuum, $C_{60}$ diamine adduct is obtained as brown-coffee powder. The reaction equation is as follows:

(iv) At room temparature and in nitrogen atmosphere, a definite amount of $C_{60}$ powder is gradually added to 1,4-diaminobutane while vigorously stirring. The color of solution turns gradually from colorless to dark brown. After all the $C_{60}$ is added, the solution is further stirred at room temperature until certainly no $C_{60}$ particles are observed. Then, the solution is poured to methanol and immediate precipitation is observbed. Precipitate is separated by filtration and centrifugation and washed with water, methanol, acetone, toluene, and ether. After drying in vacuum, $C_{60}$ diamine adduct is obtained as light brown powder. The reaction equation is as follows:

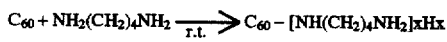

(v) In liquid nitrogen, a definite amount of $C_{60}$ is first dissolved in benzene to prepare $C_{60}$ solution. The $C_{60}$ solution is then degased and the air in the solution is replaced with nitrogen. On the other hand, 1,4-diaminobutane standard solution having a concentration of 1 mmol diamine/1 ml benzene is prepared. The standard solution is added to the $C_{60}$ solution. The solution is of dark purple color. It is then kept in liquid nitrogen for immediate freezing and then moved out and warmed to room temperature. The color solution becomes clear colorless and $C_{60}$ diamine adducts are precipitated. The precipitate is separated from the solution by centrifugation and washed with water, methanol, acetone, toluene, and ether. After drying in vacuum, $C_{60}$ diamine adduct is obtained as brown powder. The reaction equation is as follows:

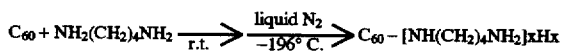

According to the present inveniton, $C_{60}$ diamine adducts are useful as polymerization monomers and can polymerize with dicarboxylic acids such as adipic acid, dicarboxylic esters such as methyl adipate or diacylchlorides such as adipyl chloride at a temperature above 170° C. and in the presence of chloroform, benzene or ethanoldiamine to produce polyamide polymers or copolymers thereof.

The following examples are illustrated to further describe the present invention.

EXAMPLE 1

At room temperature and in nitrogen atmosphere, 13.96 ml (139 mmole) 1,4-diaminobutane was added to 10 mg (1.3933 $10^{-2}$ mmole) $C_{60}$ in 35 ml benzene. The color of solution turned from purple gradually to brown and precipitation was observed immediately. The solution was stirred at room temperature for additional 24 hours to ensure the completion of reaction. The precipitate was separated from the solution by centrifugation and washed with water, methanol, acetone, toluene, and ether. After drying in vacuum, $C_{60}$ diamines adduct was obtained as brown-coffee powder. Elemental analysis showed that the product contained 5.9% nitrogen, 72.58% carbon and 3.83% hydrogen and that diamine was really added to $C_{60}$ and the number of diamine was determined to be 2 to 4. The results were further proven by the IR chromatogram shown in FIG. 1.

EXAMPLE 2

Figure 2:
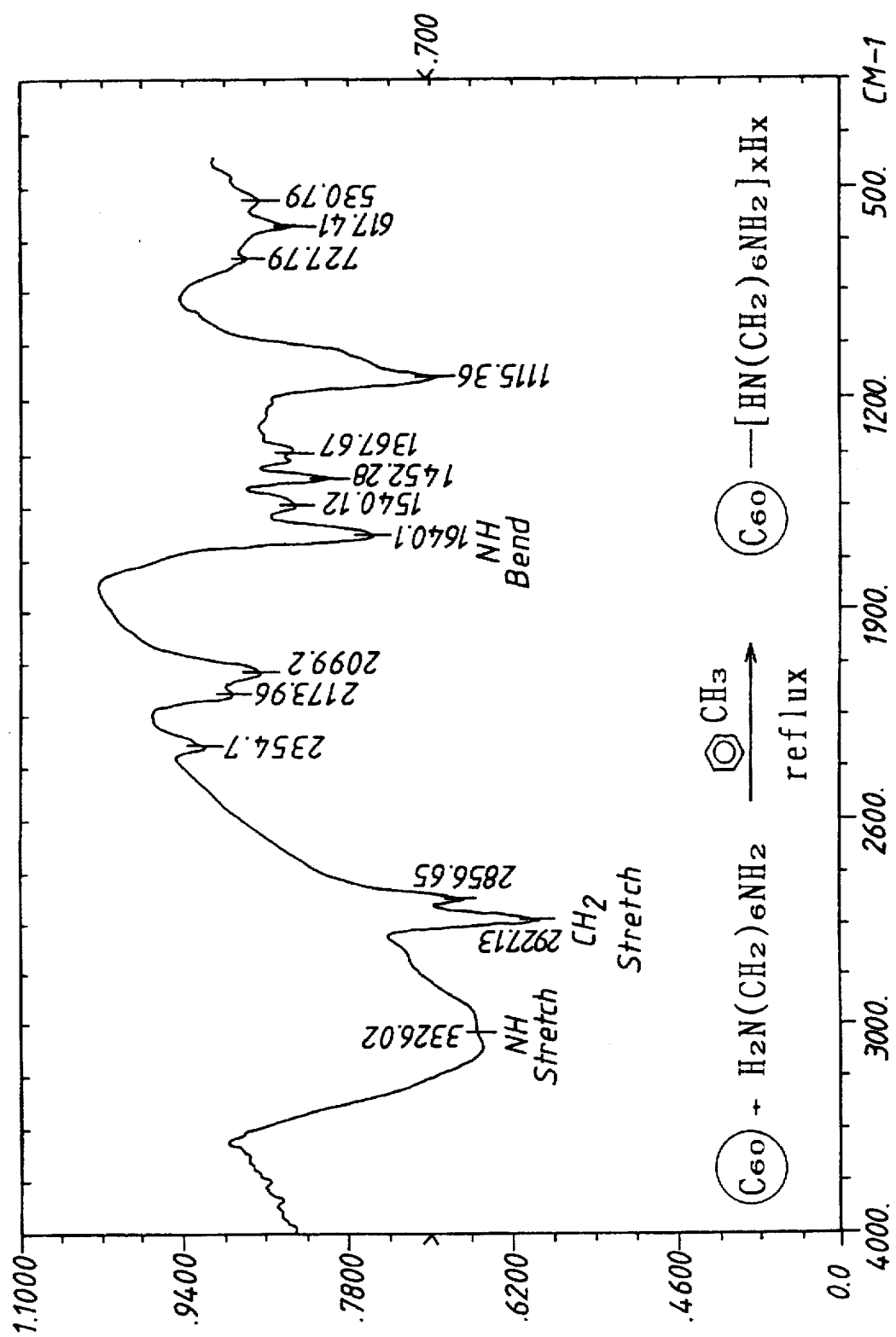
FIG. 2 shows the IR chromatogram obtained from the product of Example 2 illustrating the formation of $C_{60}$ diamine adduct.

In nitrogen atmosphere, 10 mg (1.39×$10^{-2}$ mmole) $C_{60}$ in 10 ml toluene was refluxed. 161.38 mg (1.388 mmole) 1,6-diaminohexane was added to the solution dropwise and the solution was refluxed for additional 48 hours during which the color of $C_{60}$ solution turned from dark purple gradually to completely brown. The solvent was then removed on a rotary evaporator and the residual precipitate was washed with water, methanol, acetone and ether. After drying in vacuum, $C_{60}$ diamine adduct was obtained as brown-coffee powder. Elemental analysis showed that the product contained 7.34% nitrogen, 54.10% carbon and 6.18% hydrogen and that diamine was really added to $C_{60}$ and the number of diamine was determined to be 4.5 in average. The results were further proven by the IR chromatogram shown in FIG. 2.

EXAMPLE 3

Figure 3:
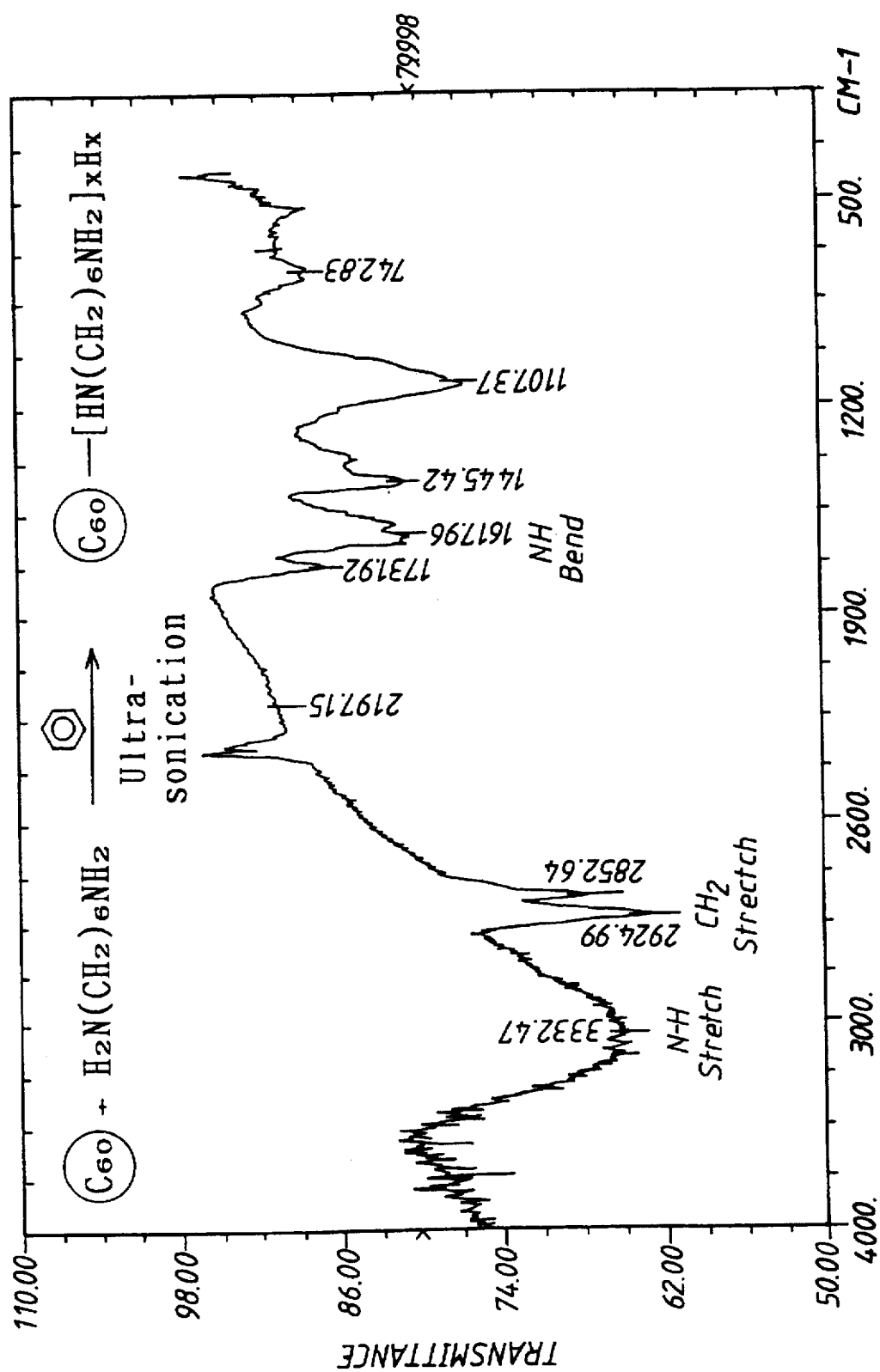
FIG. 3 shows the IR chromatogram obtained from the product of Example 3 illustrating the formation of $C_{60}$ diamine adduct.

At room temperature and in nitrogen atmosphere, 10 mg (1.39×$10^{-2}$ mmole) $C_{60}$ in 10 ml toluene and a definite amount (100 equivalents) of 1,6-diaminohexane were added to a 25 ml round-bottom flask. The solution was vigorously stirred and ultrasonicated for 10 hours. After the reaction, the precipitate was separated from the solution by centrifugationj and washed with water, methanol, acetone, toulene, and ether. After drying in vacuum, $C_{60}$ diamine adduct was obtained as brown-coffee powder. Elemental analysis showed that the product contained contained 3.81% nitrogen, 50.07% carbon and 4.87% hydrogen and that diamine was really added to $C_{60}$ and the number of diamines 5 was determined to be 2.25 in average. The results were further proven by the IR chromatogram shown in FIG. 3.

EXAMPLE 4

Figure 4:
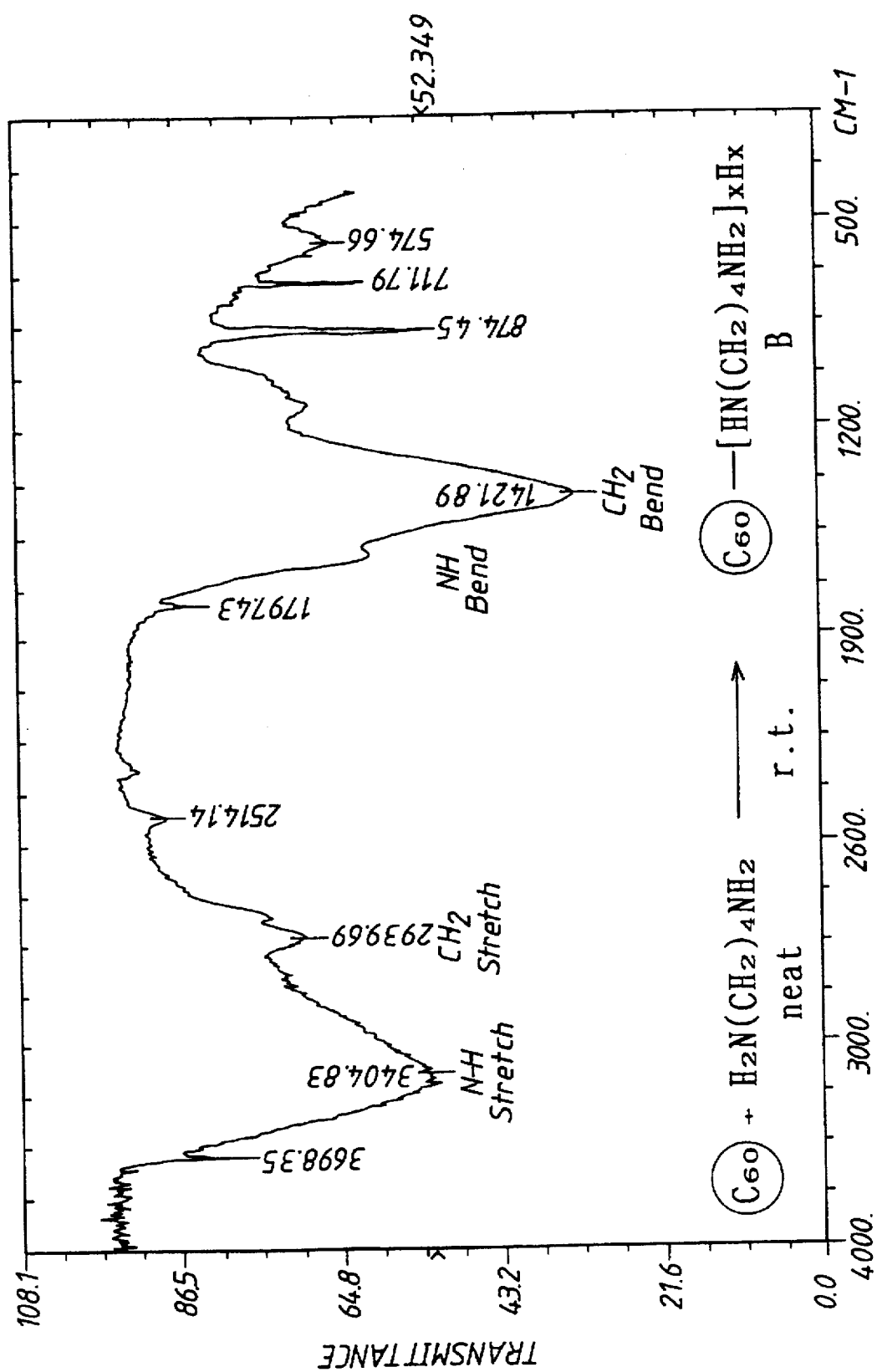
FIG. 4 shows the IR chromatogram obtained from the product of Example 4 illustrating the formation of $C_{60}$ diamine adduct.

In nitrogen atmosphere, 97.94 mg (1.11 mmole) 1,6 diamino butane was added to a test tube charged with 50 mg (6.94×$10^{-2}$ mmole) $C_{60}$ The mixture was gently stirred at room temperature for 48 hours. The color of solution turned from clear to yellow-brown then to black. After the completion of reaction, the solution was added to 5 ml ethanol and precipitation was observed immediately. The solid particles precipitated were obtained by centrifugation and washed with water, methanol, acetone, toluene, and ether. After drying in vacuum, $C_{60}$ diamine adduct was obtained as light brown powder. Elemental analysis showed that the product contained 5.84% nitrogen, 76.19% carbon and 3.32% hydrogen and that diamines was really added to $C_{60}$ and the number of diamine was determined to be 2 in average. The results were further proven by the IR chromatogram shown in FIG. 4.

EXAMPLE 5

Figure 5:
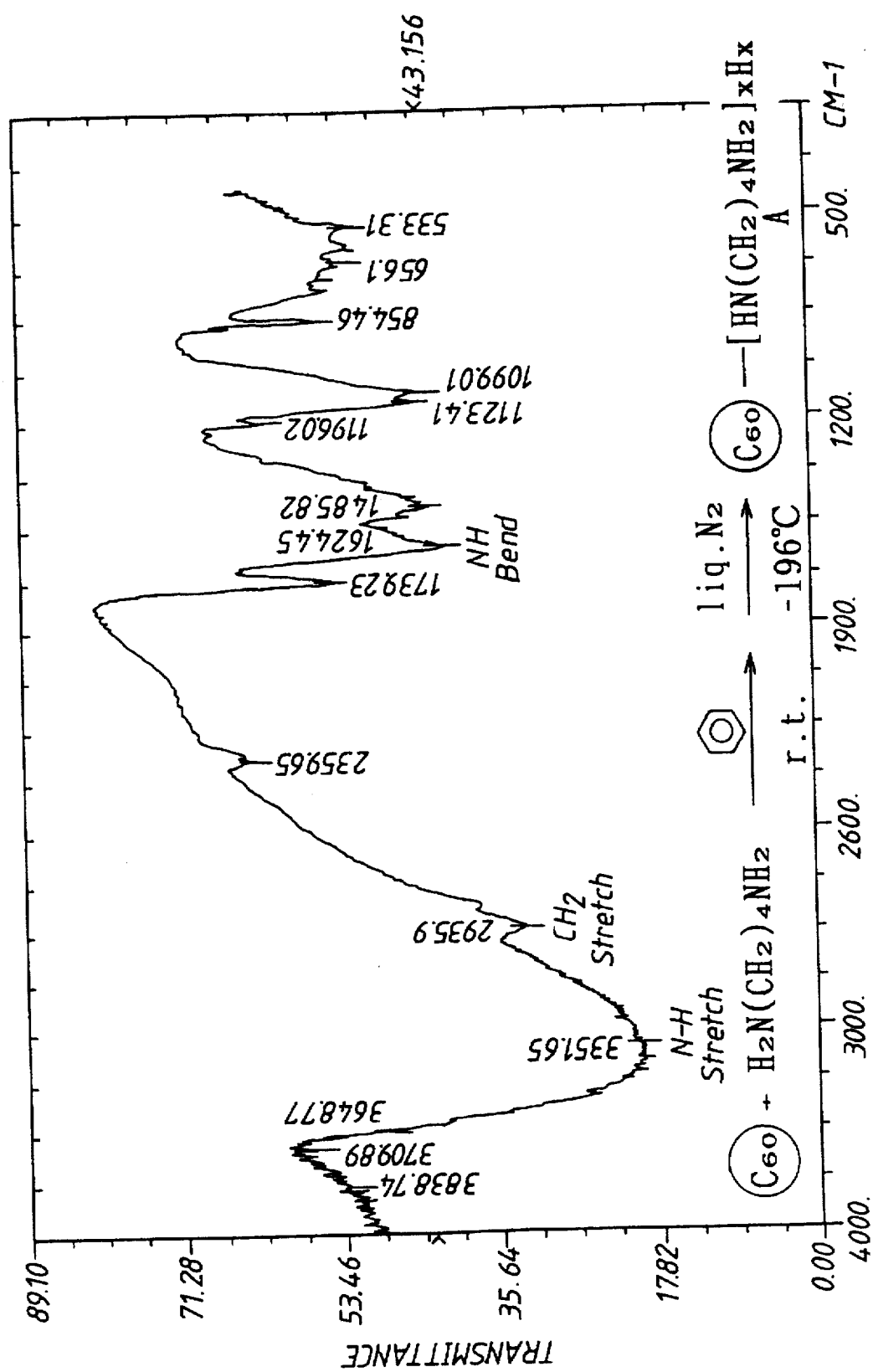
FIG. 5 shows the IR chromatogram obtained from the product of Example 5 illustrating the formation of $C_{60}$ diamine adduct.

A bottle of 1,4-diaminobutane standard solution having a concentration of 1 mmole diamine / ml benzene was prepared. 69.44 ul (6.94×$10^{-2}$ mmole) 1,4-diaminobutane standard solution equivalent to 5 equivalents of 1,4-diaminobutane was added to 10 mg (1.39×$10^{-2}$ mmole) $C_{60}$ in 10 ml benzene. At this time, the solution was of dark purple color and no reaction was observed. The solution was moved into in liquid nitrogen (−196° C.) for about 1 minute for immediate freezing and then taken out and warmed to room temperature. At this time, the color of solution became lighter and some fine solid particles were suspended in the solution. The aforementioned steps were repeated and 5 equivalents of 1,4-diaminobutane were added each time. It was found that the color of solution faded gradually through the freezing and warming up cycle and the suspended solid particles increased until the solution became colorless and no further change occured. 100 equivalents of 1,4- diaminobutane were consumed in total. Alternatively, 300 equivalents of 1,4-diaminobutane were added to $C_{60}$ in benzene. The solution was cooled down, kept for 3 minutes and then warmed to room temperature. At this time, the solution became nearly clear colorless with some precipitate. The precipitate was separated from the solution by centrifugation and washed with water, methanol, acetone, toluene and ether. After drying in vacuum, $C_{60}$ diamine adduct was obtained as brown powder. Elemental analysis showed that the product contained 7.86% nitrogen, 72.42% carbon and 4.05% hydrogen and that diamines was really added to $C_{60}$ and the number of diamine was determined to be 3.33 in average. The results were further proven by the IR chromatogram shown in FIG. 5.

EXAMPLE 6

Figure 6:
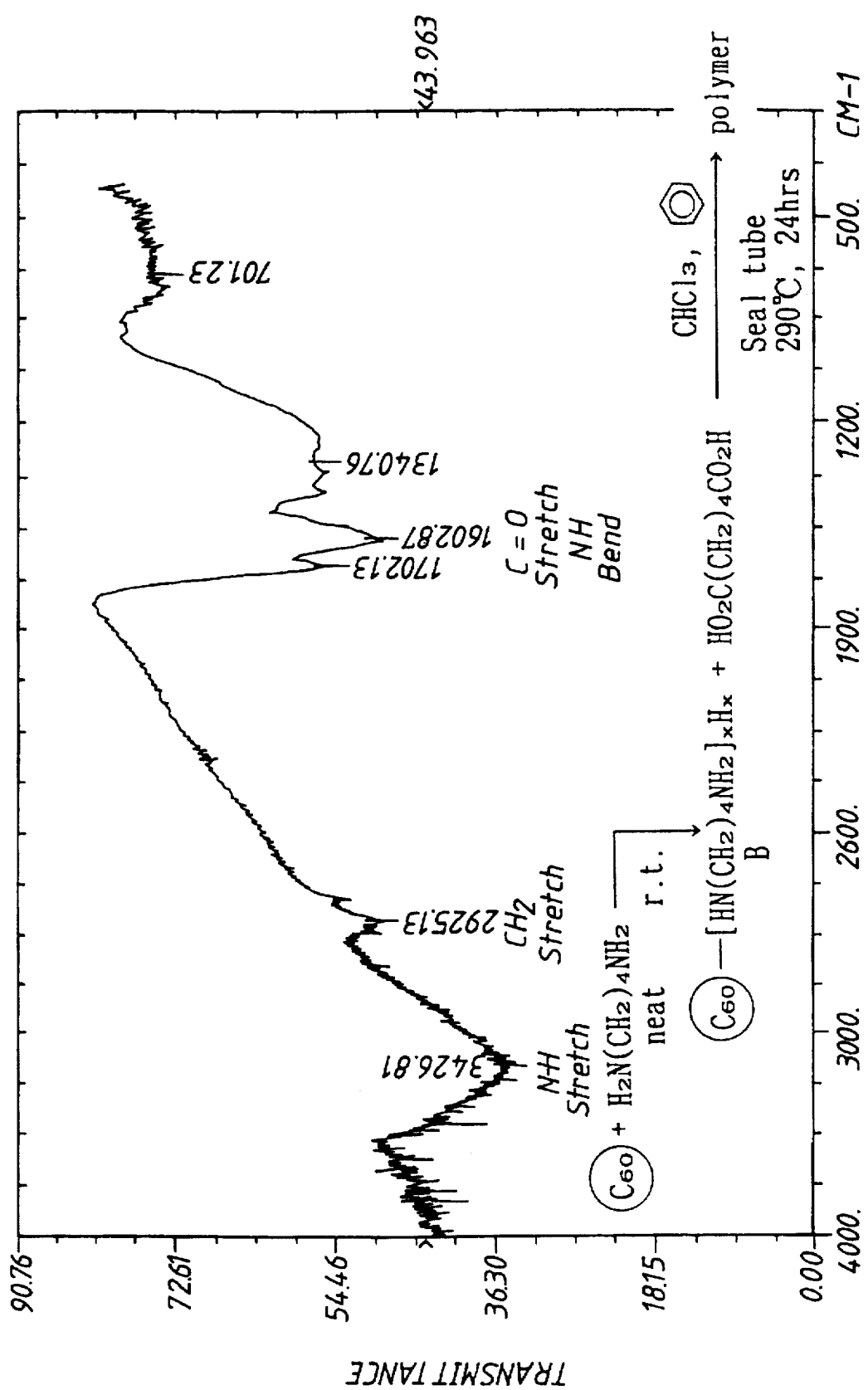
FIG. 6 shows the IR chromatogram obtained from the product of Example 6 illustrating the formation of polymide containing the $C_{60}$ diamine adduct.

At 290° C. and in the presence of chloroform ($CHCl_3$) and benzene, the $C_{60}$ diamine adduct prepared as described in Example 5 was polymerized with a dicarboxlyic acid, adipic acid ($HOOC(CH_2)_4COOH$) to produce polyamide polymer. The reaction product was identified by the IR chromatogram shown in FIG. 6.

EXAMPLE 7

Figure 7:
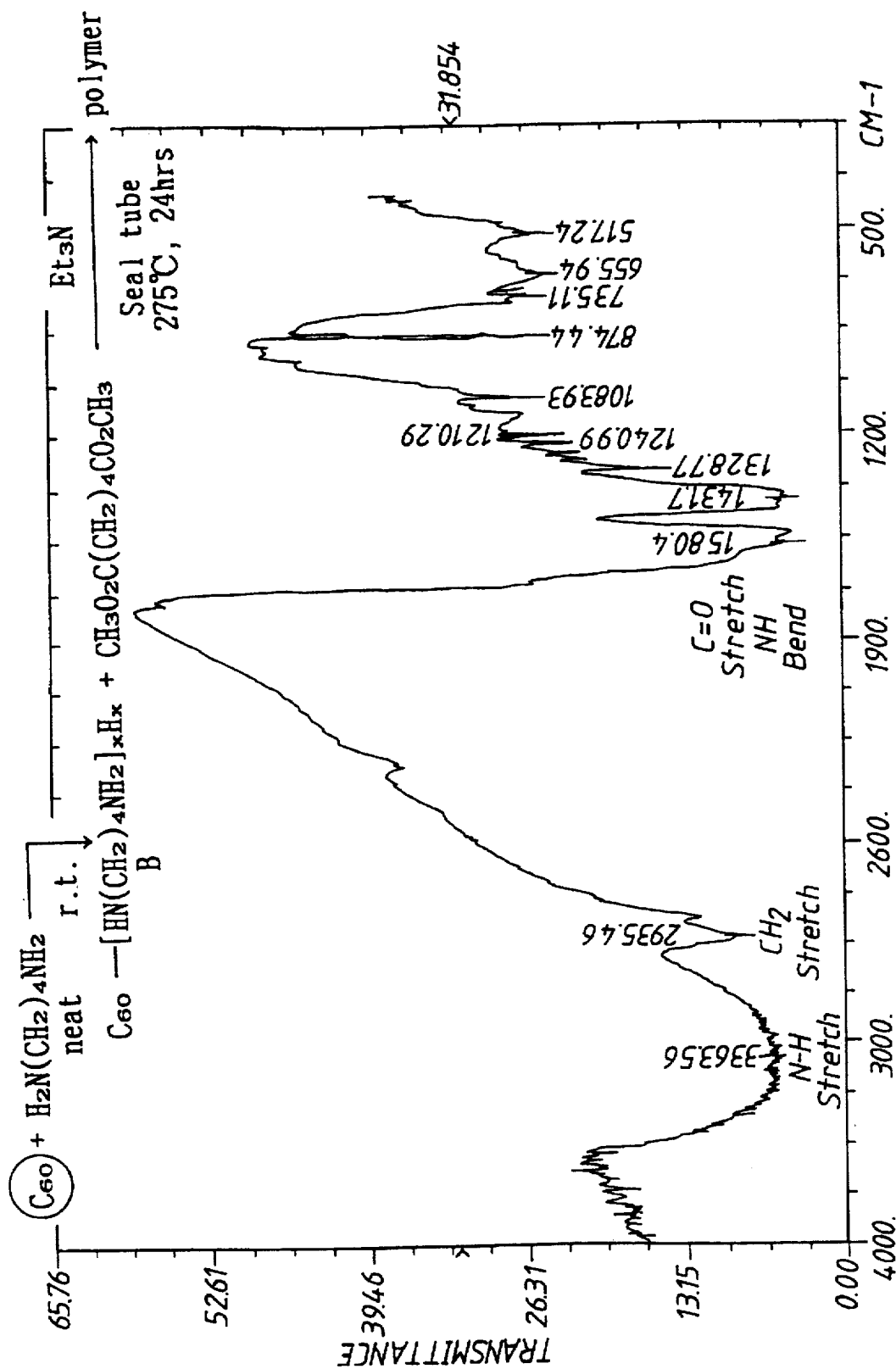
FIG. 7 shows the IR chromatogram obtained from the product of Example 7 illustrating the formation of polymide containing the $C_{60}$ diamine adduct.

At 275° C. and in the presence of triethylamine, the $C_{60}$ diamine adduct prepared as described in Example 5 was polymerized with a dicarboxlyic ester, methyl adipate $CH_3OOC(CH_2)_4COOH$) to produce polyamide polymer. The reaction product was identified by the IR chromatogram shown in FIG. 7.

EXAMPLE 8

Figure 8:
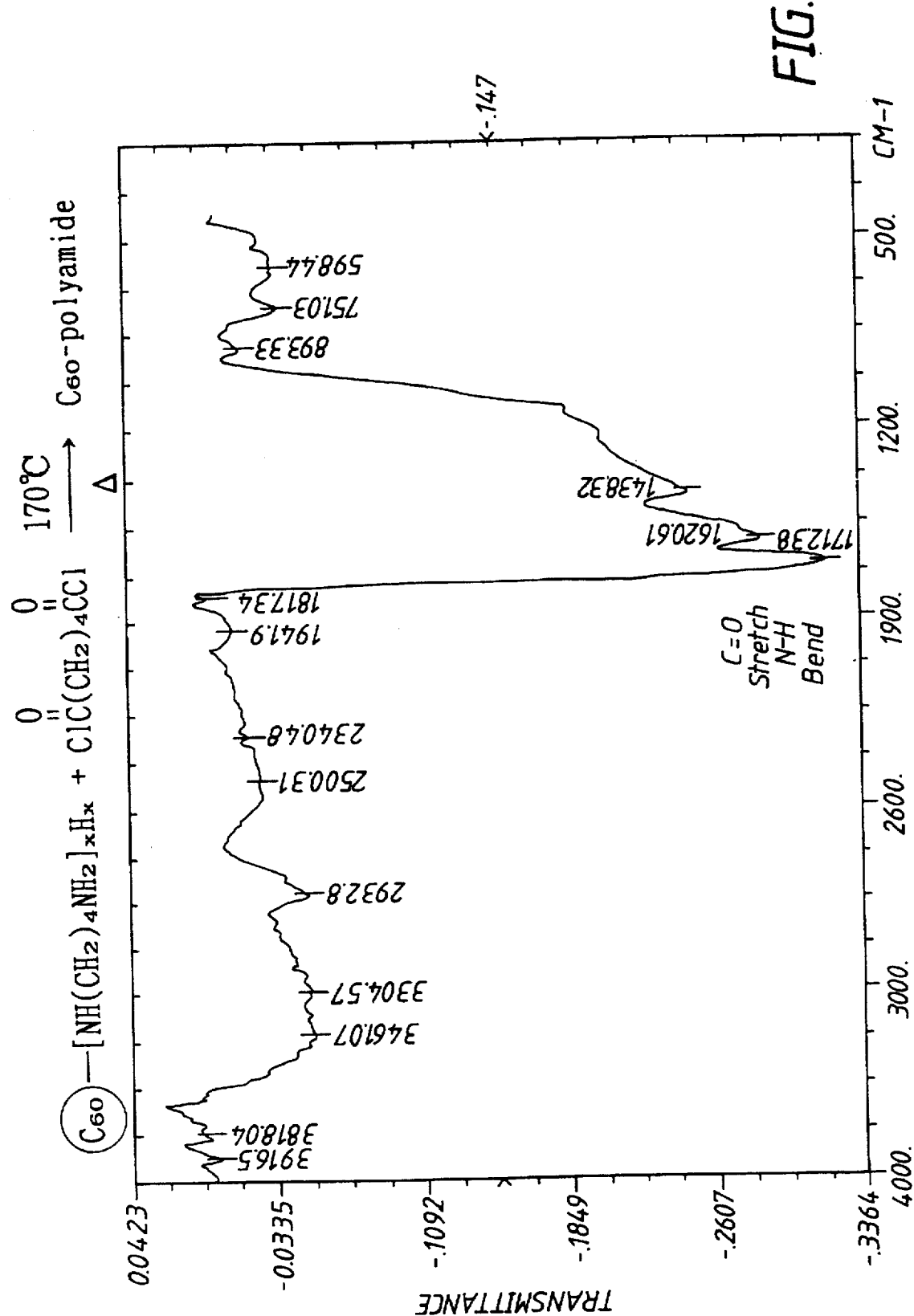
FIG. 8 shows the IR chromatogram obtained from the product of Example 8 illustrating the formation of polymide containing the $C_{60}$ diamine adduct.
Figure 9:
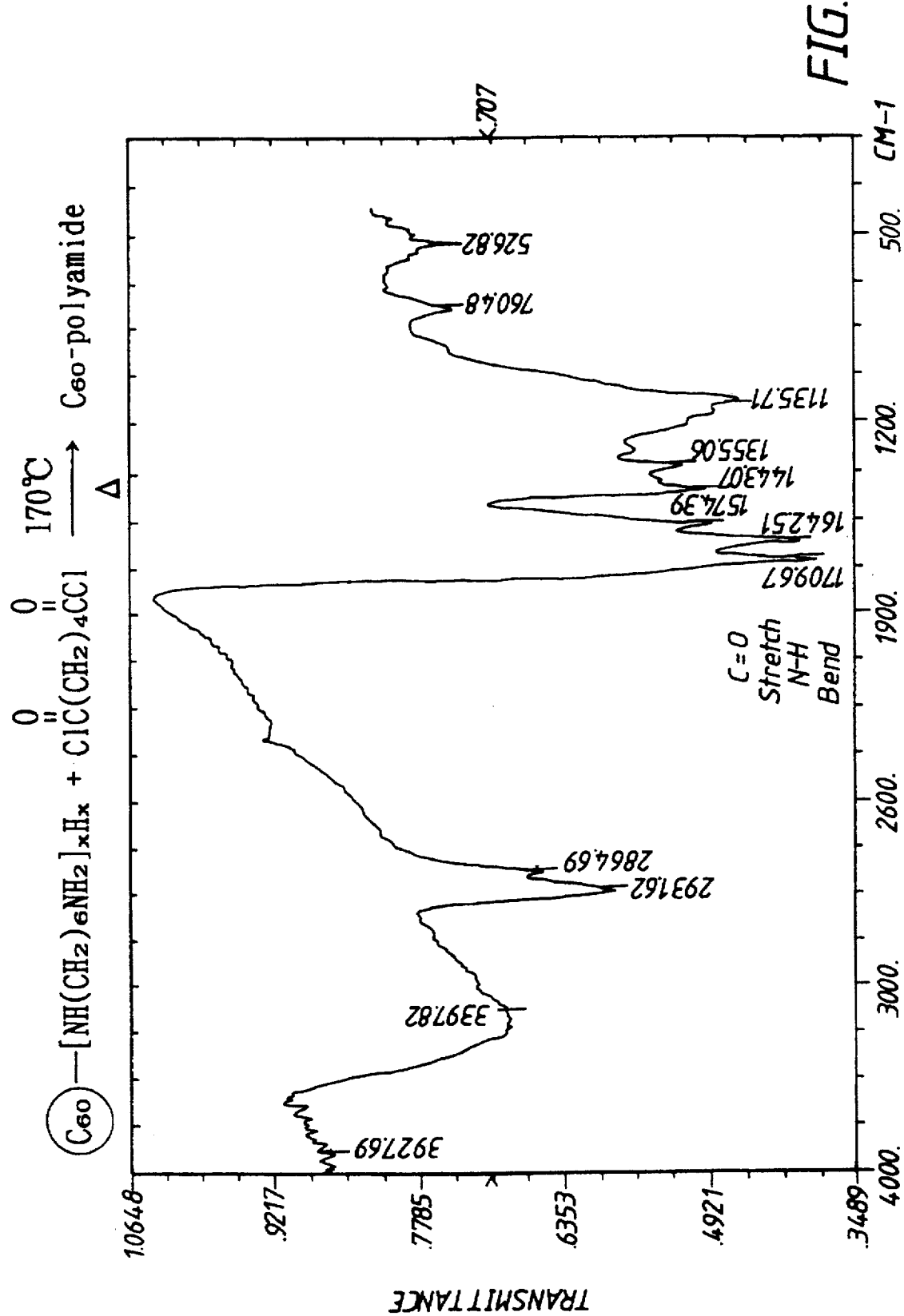
FIG. 9 shows the IR chromatogram obtained from the product of Example 9 illustrating the formation of polymide containing the $C_{60}$ diamine adduct.

At 170°, the $C_{60}$ diamine adduct prepared as described in Example 5 was polymerized with a diacylchloride, adipyl chloride ($ClOC(CH_2)_4OCCl$) to produce polyamide copolymer. The reaction product was identified by the IR chromatograms shown in FIGS. 8 and 9.

EXAMPLE 9

Figure 10:
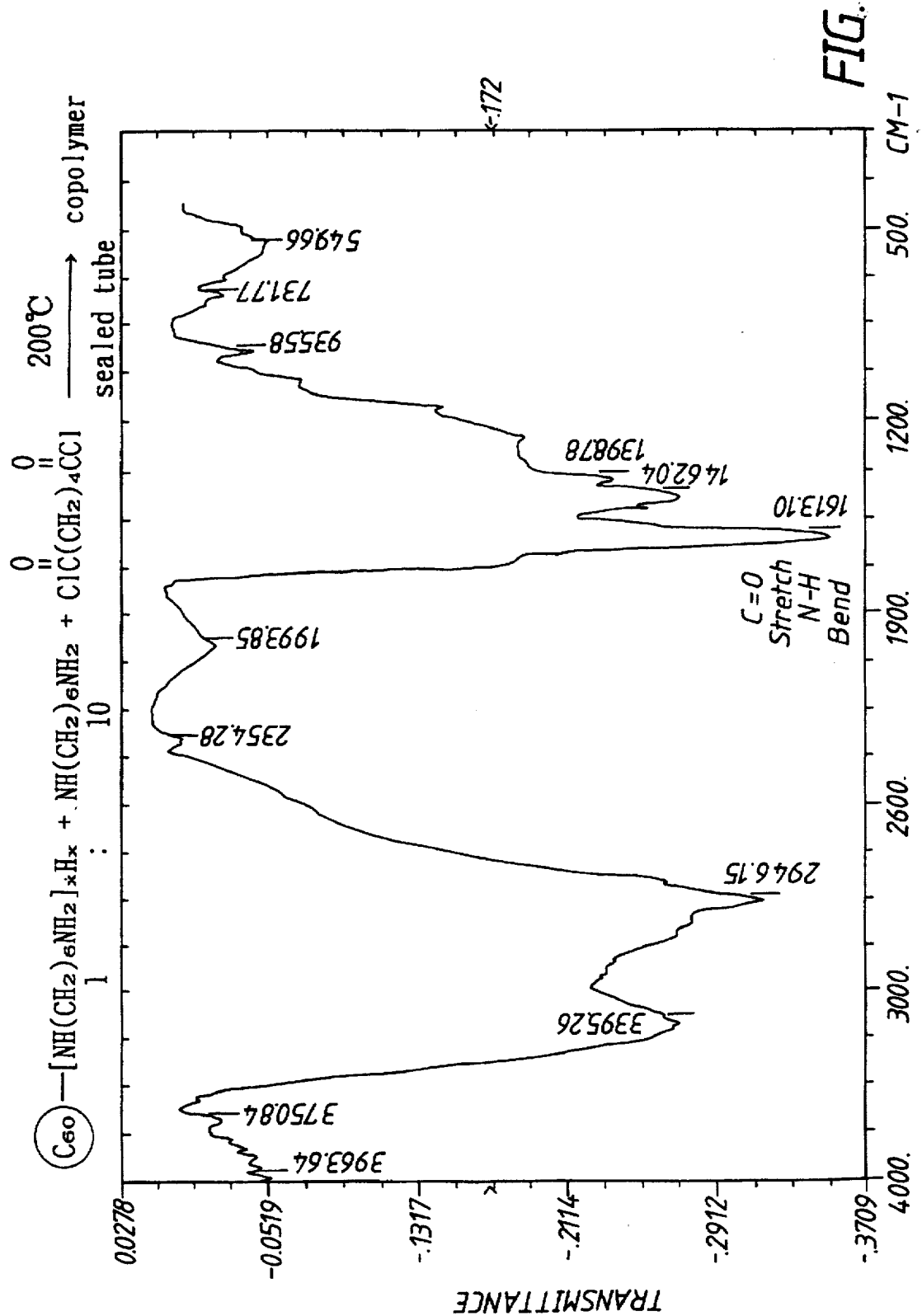
FIG. 10 shows the IR chromatogram obtained from the product of Example 10 illustrating the formation of $C_{60}$ solid diamine adducts.

At 200° C., the $C_{60}$ diamine adduct prepared as described in Example 5 was polymerized with a 1,6-diaminohexane and a diacylchloride, adipyl chloride ($ClOC(CH_2)_4OCCl$) to produce polyamide copolymer. The reaction product was identified by the IR chromatogram shown in FIG. 10.

We claim:

1. A $C_{60}$ diamine adduct having the formula $C_{60}$—[HN$(CH_2)_6NH_2$]xHx wherein $C_{60}$ in structure is a symmetrical icosahedron consisting of 12 pentagons and 20 hexagons and x is the number of diamines linked to $C_{60}$.

2. The $C_{60}$ diamine adduct according to claim 1 wherein x is between 1 and 6.

3. The $C_{60}$ diamine adduct according to claim 1 wherein x is between 2 and 4.

4. A composition comprising a mixture of $C_{60}$-diamine adducts having the formula $C_{60}$—[HN$(CH_2)_6NH_2$]xHx wherein $C_{60}$ in structure is a symmetrical icosahedron consisting of 12 pentagons and 20 hexagons and x is the average number of diamines linked to $C_{60}$.

5. The composition according to claim 4 wherein x is between 2 and 4.

6. The composition according to claim 4 wherein x is about 4.5.

7. The composition according to claim 4 wherein x is about 2.25.

8. The composition according to claim 4 wherein x is about 2.

9. The composition according to claim 4 wherein x is about 3.33.

* * * * *